(12) United States Patent
Maroy et al.

(10) Patent No.: US 8,571,283 B2
(45) Date of Patent: Oct. 29, 2013

(54) METHOD FOR SIMULTANEOUSLY EXTRACTING THE INPUT FUNCTION AND PHARMACOKINETIC PARAMETERS OF AN ACTIVE INGREDIENT

(75) Inventors: Renaud Maroy, Paris (FR); Segolene De Gavriloff, Beaugency (FR)

(73) Assignee: Commissariat a l'Energie Atomique et aux Energies Alternatives, Paris (FR)

( * ) Notice: Subject to any disclaimer, the term of this patent is extended or adjusted under 35 U.S.C. 154(b) by 294 days.

(21) Appl. No.: 13/043,969

(22) Filed: Mar. 9, 2011

(65) Prior Publication Data

US 2011/0229000 A1   Sep. 22, 2011

(30) Foreign Application Priority Data

Mar. 10, 2010   (FR) ..................................... 10 51738

(51) Int. Cl.
*G06K 9/00*   (2006.01)
(52) U.S. Cl.
USPC ........................... 382/128; 382/131; 382/132
(58) Field of Classification Search
USPC .......................................... 382/128, 131, 132
See application file for complete search history.

(56) References Cited

U.S. PATENT DOCUMENTS

| | | | | |
|---|---|---|---|---|
| 7,517,693 | B2 * | 4/2009 | Riviere et al. | 436/164 |
| 7,630,550 | B2 * | 12/2009 | Maroy et al. | 382/173 |
| 7,983,735 | B2 * | 7/2011 | Manjeshwar | 600/436 |
| 8,391,643 | B2 * | 3/2013 | Melbourne et al. | 382/294 |

FOREIGN PATENT DOCUMENTS

| | | |
|---|---|---|
| WO | WO 2007/132242 | 11/2007 |
| WO | WO 2009/019535 | 2/2009 |

OTHER PUBLICATIONS

Feng et al., 1997, "A Technique for Extracting Physiological Parameters and the Required Input Function Simultaneously from PET Image Measurements: Theory and Simulation Study", IEEE Transactions on Information Technology in Biomedicine, 1(4):243-254 (Dec. 1997).
Maroy et al., 2008, "Segmentation of Rodent Whole-Body Dynamic PET Images: An Unsupervised Method Based on Voxel Dynamics", IEEE Transactions on Medical Imaging, 27(3): 342-354 (Mar. 2008).
Webb, A., 1999, "Statistical pattern recognition, Feature selection", Statistical Pattern Recognition, London: pp. 215-226 (Dec. 1999).

* cited by examiner

*Primary Examiner* — Tom Y Lu
(74) *Attorney, Agent, or Firm* — Kenyon & Kenyon LLP (57) ABSTRACT

This extraction method in a structure of a living organism from a measurement image of the kinetics of the active ingredient comprising a plurality of regions of interest inside each of which the kinetics of the active ingredient are measured, comprises the following steps:
  determining (30) a plurality of sets of kinetics, the determined sets of kinetics being different from each other and each determined set of kinetics including several measured kinetics;
  defining (32) at least one kinetic model, parameters of the defined kinetics model being formed by the parameters of the input function and the pharmacokinetic parameters;
  estimating (34) the input function and the pharmacokinetic parameters by resolving the kinetic model defined from the determined set of kinetics; and
  deducing (36) the final input function and the final pharmacokinetic parameters.

15 Claims, 8 Drawing Sheets

METHOD FOR SIMULTANEOUSLY EXTRACTING THE INPUT FUNCTION AND PHARMACOKINETIC PARAMETERS OF AN ACTIVE INGREDIENT

CROSS REFERENCE TO RELATED APPLICATION

The present application claims priority to Application No. 1051738, filed in France on Mar. 10, 2010.

FIELD OF INVENTION

The present invention relates to a method for simultaneously extracting the input function and pharmacokinetic parameters of an active ingredient in a structure of a living organism from a measurement image of the kinetics of the active ingredient in the structure obtained by an imaging device, the image comprising a plurality of regions of interest inside each of which the kinetics of the active ingredient are measured.

BACKGROUND INFORMATION

In vivo molecular imaging makes it possible to measure the pharmacokinetic properties of an active ingredient in intact animals and humans. Molecular imaging encompasses nuclear techniques and optical techniques. Among nuclear techniques, position emission tomography (PET) and single photon emission computed tomography (SPECT) are the most sensitive techniques and the only ones to offer quantitative measurements.

The quantification of the measurements with PET or SPECT to study an active ingredient requires the intravenous injection of a radioactive tracer adapted to the study of said active ingredient. An image of the distribution of the tracer, and therefore the active ingredient, is then reconstructed from a temporal sequence of PET or SPECT images for measuring the concentration of the tracer.

The post-processing of the PET or SPECT image generally requires three steps to access the pharmacokinetic parameters. First, regions of interesting delimiting the pharmacokinetic organs, called pharmaco-organs, must be defined on the temporal sequence of PET or SPECT images, or on a morphological image recalibrated with the temporal sequence of PET or SPECT images. Then, the kinetics of the pharmaco-organs, i.e. the temporal activity curves of the tracer corresponding to the variations over time of the concentration of the tracer, must be extracted. Lastly, a physiological kinetic model can be defined, based on the kinetics and the concentration of the tracer in the plasma, making it possible to calculate the pharmacokinetic parameters of interest for the practitioner.

The extraction of the pharmacokinetic parameters through imaging using a tracer is therefore the final step providing access to information on the processing of the tracer by the body, thus able to provide information on the effectiveness of a drug or the evolution of a pathology.

Methods are known that make it possible to estimate the pharmacokinetic parameters and the blood concentration of the non-metabolized tracer as a function of time, called input function, from the extracted kinetics. Indeed, the input function is necessary to know the pharmacokinetic parameters, but it is not always directly visible in the image.

However, the pharmacokinetic parameters extracted using these methods suffer from a very strong bias when they do not benefit from additional information in the form of venous or arterial collection. Moreover, the existence of such a restriction makes these methods applicable only to a very small number of tracers.

SUMMARY

The invention aims to propose a minimally invasive method making it possible to directly extract, from the image, with the smallest possible bias, the pharmacokinetic parameters simultaneously with the input function.

To that end, the invention relates to a method of the aforementioned type, characterized in that it comprises the following steps:
  determining a plurality of sets of kinetics from the measured kinetics, the determined sets of kinetics being different from each other and each determined set of kinetics including several measured kinetics;
  defining at least one kinetic model, parameters of the defined kinetics model being formed by the parameters of the input function and the pharmacokinetic parameters;
  estimating, for each determined set of kinetics, the input function and the pharmacokinetic parameters by resolving the kinetic model defined from the determined set of kinetics; and
  deduce the final input function and the final pharmacokinetic parameters from estimated input functions and estimated pharmacokinetic parameters.

The inventive method can include one or several of the following features:
  the step for determining the plurality of sets of kinetics comprises the following steps:
  forming all of possible sets of kinetics from the measured kinetics; and
  selecting, from the formed sets of kinetics, a predetermined number of sets of kinetics, this step comprising the following steps:
    evaluating, for each formed set of kinetics, a criterion for selecting sets of kinetics making it possible to assess their risk of introducing errors into the estimation of the input function and the pharmacokinetic parameters;
    ranking the formed sets of kinetics according to a rule of the maximum selection criterion; and
    choosing a predetermined number of the first ranked sets of kinetics;
  the criterion for selecting sets of kinetics makes it possible to select the sets of kinetics whereof the measured kinetics are different from each other in terms of shape and/or amplitude, and/or whereof the measured kinetics are not very affected by the partial volume effect and/or whereof the measured kinetics have a strong signal to noise ratio;
  the defined kinetic model takes into account the metabolization of the active ingredient in the structure of the imaged living organism;
  the step for estimating the input function and the pharmacokinetic parameters is done several times for each determined set of kinetics so as to find the different solutions for the defined kinetic model;
  the determined sets of kinetics comprise sets of kinetics including the same number of measured kinetics;
  the determined sets of kinetics comprise sets of kinetics including a different number of measured kinetics;
  the step for estimating the input function and the pharmacokinetic parameters comprises the minimization of a cost function making it possible to evaluate the dissemblance between the determined set of kinetics and the defined kinetic model;

the step for estimating the input function and the pharmacokinetic parameters is carried out according to an iterative loop in which the input functions and pharmacokinetic parameters estimated during an iteration make it possible to determine the initialization of the input functions and pharmacokinetic properties estimated in the following iteration and/or to contribute constraints on the input functions and pharmacokinetic parameters estimated in the following iteration;

the step for defining at least one kinetic model comprises the definition of a plurality of kinetic models, parameters of the defined kinetic models being formed by the parameters of the input function and the pharmacokinetic parameters;

the step for estimating the input function and the pharmacokinetic parameters comprises, for each determined set of kinetics, the resolution of the kinetic models defined from the determined set of kinetics, and the method comprises a step for choosing, among the plurality of kinetic models, an optimal kinetic model in terms of compromise between suitability of the kinetic model for the data and the low number of parameters of the input function and the pharmacokinetic parameters to be extracted;

the step for defining at least one kinetic model comprises, aside from the choice of the form of the kinetic model, the introduction into the kinetic model of constraints resulting from a priori knowledge not related to arterial samples done on the imaged living organism, the constraints making it possible to set at least one parameter of the kinetic model such as the vascular fractions of the regions of interest;

the step for estimating the input function and the pharmacokinetic properties comprises the introduction into the resolution of the kinetic model of constraints resulting from a priori knowledge not related to arterial samples done on the imaged living organism, the constraints making it possible to add known terms into the resolution of the kinetic model such as terms taking into account a priori knowledge of the vascular fractions of the regions of interest and/or the distribution volume of the active ingredient over a given population; and the measurement image of the kinetics of the active ingredient in the structure is obtained from a temporal sequence of three-dimensional images obtained by position emission tomography or by single photon emission computed tomography; and the step for deducing the final input function and the final pharmacokinetic parameters is done by calculating the mean or the median of the parameters of the estimated input functions and the estimated pharmacokinetic parameters.

The invention also relates to an information storage medium comprising a code for simultaneously extracting the input function and the pharmacokinetic parameters of an active ingredient in a structure of a living organism from a measurement image of the kinetics of the active ingredient in the structure obtained by an imaging device, the image comprising a plurality of regions of interest inside each of which the kinetics of the active ingredient are measured, characterized in that the code comprises instructions to:

determine a plurality of sets of kinetics from the measured kinetics, the determined sets of kinetics being different from each other and each determined set of kinetics including several measured kinetics;

define at least one kinetic model, parameters of the defined kinetic model being formed by the parameters of the input function and the pharmacokinetic parameters;

estimate, for each determined set of kinetics, the input function and the pharmacokinetic parameters by resolving the kinetic model defined from the set of determined kinetics; and deducing the final input function and the final pharmacokinetic parameters from estimated input functions and estimated pharmacokinetic parameters.

The invention also relates to a device intended to simultaneously extract the input function and the pharmacokinetic parameters of an active ingredient in a structure of a living organism from a measurement image of the kinetics of the active ingredient in the structure obtained by an imaging device, the image comprising a plurality of regions of interest inside each of which the kinetics of the active ingredient are measured, characterized in that it comprises:

an imaging device; and a data processing system connected to the imaging device and comprising:

means for determining a plurality of sets of kinetics from measured kinetics, the determined sets of kinetics being different from each other and each determined set of kinetics including several measured kinetics;

means for defining at least one kinetic model, parameters of the defined kinetic model being formed by the parameters of the input function and the pharmacokinetic parameters;

means for estimating, for each determined set of kinetics, the input function and the pharmacokinetic parameters by resolving the defined kinetic model from the determined set of kinetics; and means for deducing the final input function and the final pharmacokinetic parameters from estimated input functions and estimated pharmacokinetic parameters.

The invention will be better understood upon reading the following description, provided solely as an example and with reference to the appended drawings.

DETAILED DESCRIPTION

The inventive method consists of simultaneously extracting the input function and the pharmacokinetic parameters of an active ingredient from a measurement image of the kinetics of the active ingredient.

To that end, a radioactive tracer, e.g. FDG, corresponding to the studied active ingredient is administered, for example by intravenous injection, and is conveyed by the blood into a structure of a living organism, for example a human subject's brain.

Any structure of an organism is considered a system that acts on the behavior of the tracer. The fate of the tracer in the studied structure is thus modeled by a compartment model, as well be explained in more detail later. In this model, the different states of the tracer are modeled by compartments, for example a compartment showing the intact state of the tracer in the plasma, a compartment showing the metabolized state of the tracer in the blood, a compartment showing the free state of the tracer in the structure, a compartment showing the non-specific bonded state of the tracer in the structure, a compartment showing the specific bonded state of the tracer in the structure, etc., in which the tracer is present at a certain concentration. The model is also characterized by transfer speeds of the tracer between compartments. The number of compartments and their nature depend on the type of tracer.

Knowing the concentrations of the tracer in each compartment and the transfer speeds of the tracer between compartments, these transfer speeds forming the pharmacokinetic parameters of the tracer, makes it possible to go back up to physiological quantities, such as for example the affinity of the tracer to its target, the glucose consumption of the structure, etc. The measurement of the radioactive concentration of the tracer is only a result of the hidden treatment of the tracer by the structure and is generally given by the weighted sum of the concentrations of the tracer in the different compartments.

In order to escalate radioactive concentration measurements from the tracer to the parameters of the model, it is necessary to know the tracer concentration available to the structures, which is the concentration of non-metabolized tracer in the blood plasma as a function of time and is called the input function.

Figure 1:
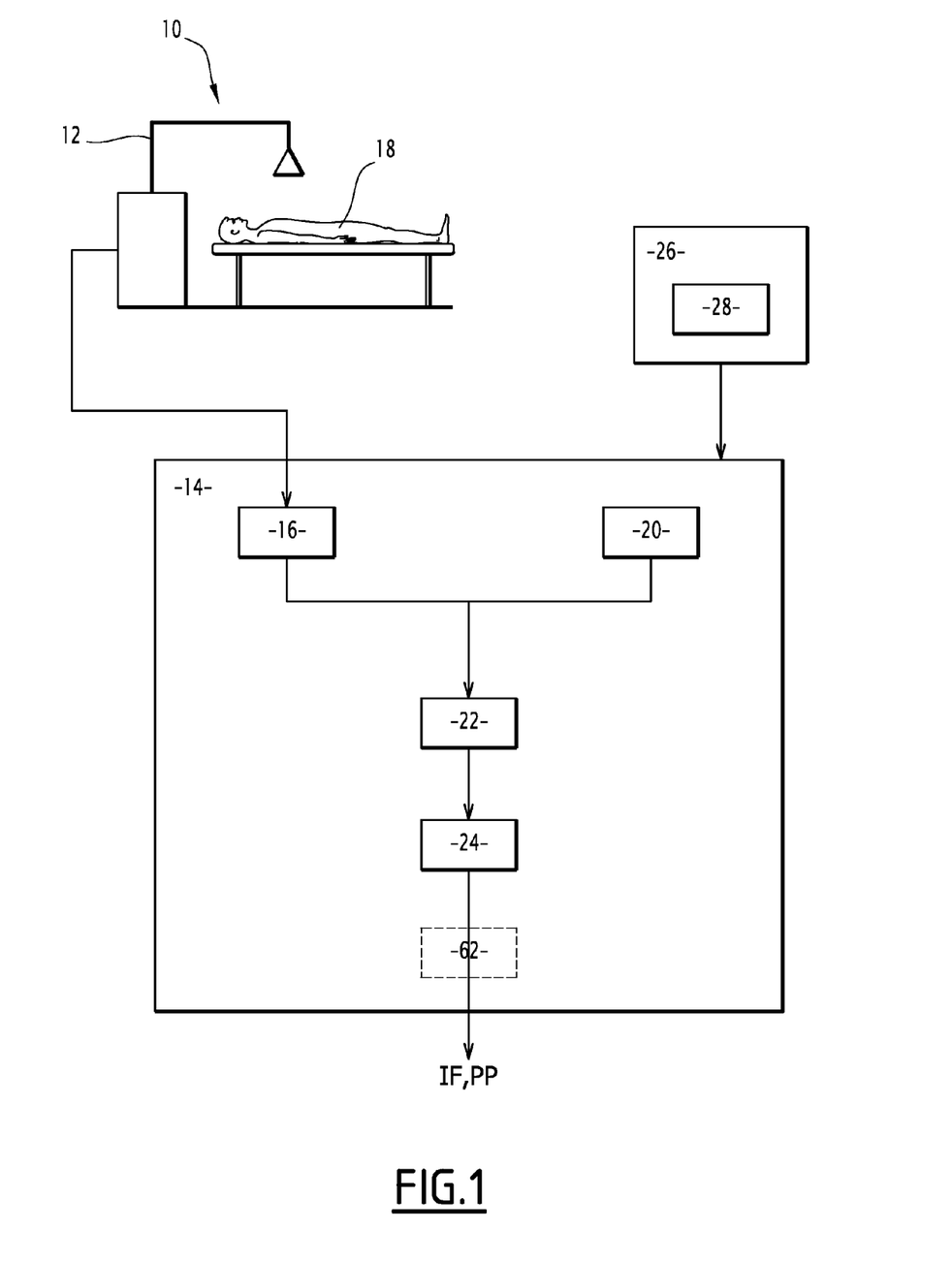
FIG. 1 is a diagrammatic view of a device implementing the inventive method.

FIG. 1 shows a device 10 making it possible to simultaneously extract the input function FE and the pharmacokinetic properties PP of an active ingredient using a radioactive tracer corresponding to the studied active ingredient.

The device 10 comprises an imaging device 12 and a data processing system 14 connected to the imaging device 12.

The data transfer system 14 comprises means 16 connected to the imaging device 12 to determine a plurality of sets of kinetics from kinetics of the tracer measured in a structure of a living organism 18 owing to the imaging device 12, and means 20 for defining at least one kinetic model.

A set of I kinetics can be defined as a vector with I components in which each component is formed by a kinetic measured in a temporal sequence of measurement images within a region of interest delineating the considered structure.

A kinetic model for a region of interest i can be defined as a model of the kinetics of the tracer in that region, i.e. a model of the variation as a function of time of the concentration of the tracer in the region, some of the parameters of the model being formed by the parameters of the input function and the pharmacokinetic parameters.

The data transfer system 14 comprises means 22 connected to the determination means 16 and to the definition means 20 to estimate the input function and the pharmacokinetic parameters, and means 24 connected to the estimating means 22 to deduce the final input function and the final pharmacokinetic parameters.

The different means 16, 20, 22, and 24 of the data processing system 14 are implemented using an information storage medium 26 comprising a code 28 including instructions, each instruction respectively corresponding to each of the means 16, 20, 22 and 24.

Figure 2:
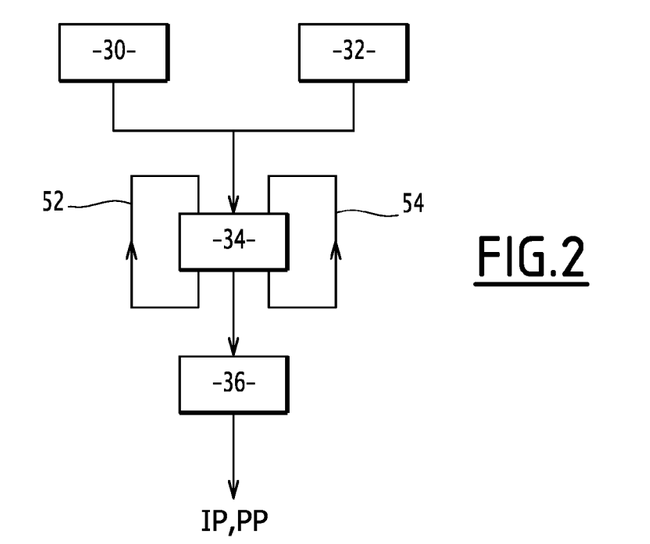
FIG. 2 is a flowchart showing the main steps of the inventive method.

As illustrated in FIG. 2, the method according to the invention comprises four main steps:
- a first step 30 intended to determine the plurality of sets of kinetics and done using the determination means 16 (FIG. 1);
- a second step 32 intended to define the kinetic model and done using the definition means 20 (FIG. 1);
- a third step 34 intended to estimate the input function and the pharmacokinetic properties by resolving the kinetic model defined in step 32 from sets of kinetics determined in step 30, and done using the estimating means 22 (FIG. 1); and
- a fourth step 36 intended to deduce the final input function and the final pharmacokinetic parameters from input functions and pharmacokinetic parameters estimated in step 34, and done by the deducing means 24 (FIG. 1).

The four main steps 30, 32 34, and 36 of the inventive method are explained below.

Figure 3:
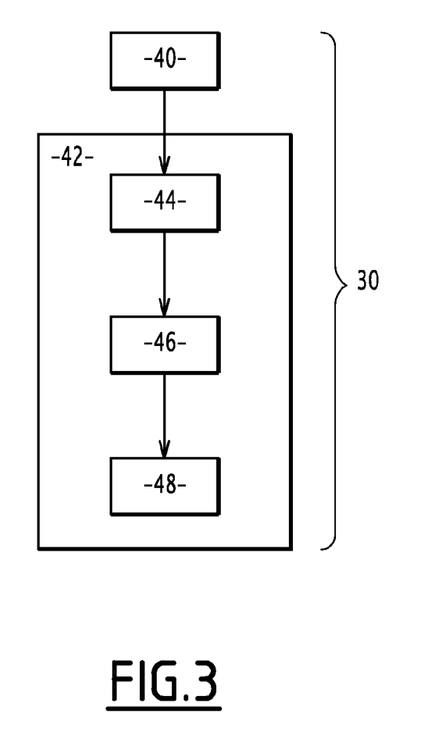
FIG. 3 is a flowchart showing the secondary steps of the first main step of FIG. 2.

In reference to FIG. 3, the first main step 30 of determining a plurality of sets of kinetics itself comprises four secondary steps.

Initially, a radioactive tracer corresponding to the studied active ingredient is injected within a structure of a living organism 18 and a measurement image of the kinetics of the tracer in the structure is obtained using the imaging device 12.

The measurement image is obtained from a temporal sequence of three-dimensional measurement images of the concentration of the tracer in the structure, which themselves are obtained by position emission tomography (PET) or single photon emission computed tomography (SPECT).

Using any suitable algorithm for segmenting images, the obtained image is partitioned into a plurality O of regions of interest.

The kinetics of the tracer are then measured inside each of the regions of interest, for example using any suitable algorithm for correcting the partial volume effect, thus leading to O measured kinetics of the tracer.

During a first secondary step 40, all of the possible sets of kinetics are formed from the O measured kinetics so that all of the sets of kinetics are different from each other and each set of kinetics includes several measured kinetics, i.e. at least two measured kinetics.

$$\sum_{I=2}^{O} C_O^I$$

Let I be the number of kinetics per set, with $2 \leq I \leq O$, so a total of sets of 1 kinetics are formed.

A second secondary step 42 then makes it possible to select, among the sets of kinetics formed, a predetermined number of sets of kinetics.

Indeed, consider a set r of I kinetics. The estimation of the input function and the pharmacokinetic parameters will be better as:

the I kinetics of the set r are different from each other, both in terms of shape and amplitude;

the I kinetics of a set r are not very affected by the partial volume effect; and the I kinetics of the set r have a strong signal to noise ratio.

For example, some of the kinetics of the set r can result from the same functional assembly, or from two different assemblies but with similar functions, and therefore have a high likelihood of being similar. The selection step 42 thereby prevents the selection of the set r including such kinetics.

The selection step 42 itself comprises three sub-steps.

A first sub-step 44 consists of assessing, for each set of kinetics formed in the formation step 40, a criterion $\Psi$ for selecting sets of kinetics making it possible to assess their risk of introducing errors into the estimate of the input function and the pharmacokinetic parameters:

$$\psi(\{Y_i\}_{1 \le i \le I}) = \frac{1}{I-1} \sum_{i=1}^{I-1} \left( \omega_1 \frac{1}{w_i^2} \frac{1}{I-i} \sum_{j=i+1}^{I} \left( \frac{\omega_2 \left( \frac{Y_i(t)}{\|Y_i\|} - \frac{Y_j(t)}{\|Y_j\|} \right)^2 + \omega_3 (\|Y_i\| - \|Y_j\|)^2 +}{\omega_4 \sum_{t=1}^{T} \frac{Y_i^2(t)}{v_{i,t}}} \right) \right)$$

with $w_i$ the collection ratio of the region i, i.e. the proportion of the signal effectively coming from the structure i that contributes to the average measurement of activity concentration in the region i at time t, accounting for the effect on the kinetics $Y_i$ by the partial volume effect, $v_{i,t}$ the variance of the error committed due to the statistical noise in the image on the estimation of $Y_i(t)$, and $\omega_1$, $\omega_2$, $\omega_3$, $\omega_4$, weights reflecting the relative importance respectively assigned to the effect on the kinetics $Y_i$ by the partial volume effect, the difference between the shapes of the kinetics, the difference between the norms of the kinetics, and the signal to noise ratio of the kinetics.

A second sub-step 46 then consists of ranking all of the sets of kinetics formed in the formation step 40 according to a rule of the maximum selection criterion, i.e. the sets of kinetics formed are sorted by decreasing order of $\Psi$.

A third sub-step 48 consists of choosing the predetermined number of sets of kinetics among the first sets of kinetics ranked in sub-step 46.

When a user chooses a maximum number of sets of kinetics to use to estimate the input function and the pharmacokinetic parameters, for example 100, then sub-step 48 consists of choosing the 100 best sets of kinetics according to $\Psi$, the other sets of kinetics not being used for the estimation.

The second main step 32 makes it possible to define at least one kinetic model, parameters of the defined kinetic model being formed by the parameters of the input function and the pharmacokinetic parameters.

Figure 4:
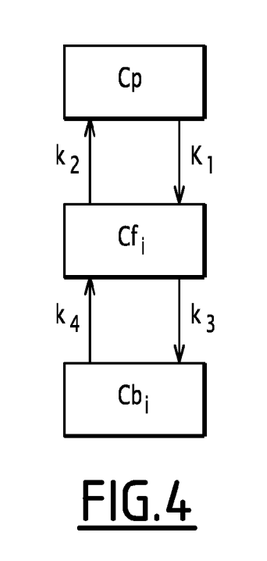
FIG. 4 is a diagrammatic view of an example of compartmental modeling of the physiological process of interaction between a tracer and a region of interest.

As previously mentioned, the physiological interaction processes between the tracer and a region of interest i are modeled by a compartment model.

FIG. 4 shows an example of a model with three compartments and four pharmacokinetic parameters.

The tracer passes through the cellular barrier with a rate constant $K_1$ and can, in the same way, pass back through the barrier to return into the blood with a rate constant $k_2$. It is transformed or binds to a receptor in the cells with a rate constant $k_3$. If this transformation or bond is reversible, the inverse transformation or dissociation is characterized by a speed constant $k_4$.

The three studied compartments are the plasma-serum compartment Cp, the free compartment $Cf_i$ of the region i, and the bonded compartment $Cb_i$ of the region i.

Let Cp(t), $Cf_i(t)$ and $Cb_i(t)$ be the concentrations of the tracer in each of these three compartments.

Then the variations of the concentrations of the tracer in the different compartments are written:

$$\frac{dCf_i(t)}{dt} = K_1 Cp(t) - (k_2 + k_3)Cf_i(t) + k_4 Cb_i(t)$$

$$\frac{dCb_i(t)}{dt} = k_3 Cf_i(t) - k_4 Cb_i(t)$$

Let $Ct_i(t)$ be the concentration of the tracer in the tissue of the region i:

$$Ct_i(t) = Cf_i(t) + Cb_i(t)$$

The solution of $Ct_i(t)$ is given by:

$$Ct_i(t) = (Cp \otimes h_i)(t)$$

where $h_i(t)$ is the response function of the region i to the non-metabolized tracer.

The method according to the invention proposes to take into account the possible metabolization of the tracer, thereby making it possible to extend the application thereof to a large number of tracers.

Assuming that the tracer is metabolized by the imaged living organism 18 in M radio-marked metabolites, let $Ca_m(t)$ be the kinetics of the metabolite m of the tracer in the artery, $Cp_m$ the blood concentration of the metabolite m of the tracer, and $h_{i,m}$ the response function of the region i to the metabolite m of the tracer.

The kinetic model $C_i(t)$ in the region i is then written:

$$C_i(t) = Vb_i \times Ca(t) + (1 - Vb_i) \times (Cp \otimes h_i)(t) + \sum_{m=1}^{M} (Vb_i \times Ca_m(t) + (1 - Vb_i) \times (Cp_m \otimes h_{i,m})(t))$$

with $Vb_i$ the fraction of blood in the region i and Ca(t) the kinetics of the non-metabolized tracer in the artery.

The third main step 34 makes it possible to estimate, for each set of kinetics determined in step 30, the input function and the pharmacokinetic parameters by resolving the defined kinetic model $C_i(t)$ from the determined set of kinetics.

To that end, the method uses any suitable algorithm making it possible to minimize a cost function $d(\{Y_i\}_{1 \le i \le I}, \{C_i\}_{1 \le i \le I})$ making it possible to assess the dissemblance between the I measured kinetics $\{Y_i\}_{1 \le i \le I}$ of the determined set of kinetics and the I corresponding kinetic models $\{C_i\}_{1 \le i \le I}$.

The fourth main step 36 makes it possible to deduce the final input function and the final pharmacokinetic parameters from input functions and pharmacokinetic parameters estimated in step 34, for example by calculating the mean or median of the parameters of the estimated input functions and the estimated pharmacokinetic parameters.

The noise and the partial volume effect that affect the measured kinetics generate a substantial bias on the estimates of the input function and the pharmacokinetic parameters. This bias generally increases when the number of parameters to be estimated increases.

The method according to the invention offers several strategies to reduce the bias on the estimates.

A first strategy consists of constraining the system by introducing terms taking into account the a priori knowledge on the parameters of the kinetic model, on the functions of parameter groups, on the shape of the input or arterial function, or also on the arterial or plasmatic kinetics of the different metabolites.

These terms can comprise terms taking into account measurements of metabolites, terms resulting from an analysis on the population (for example a mean and a standard deviation on the vascular fractions $Vb_i$ of the regions of interest i), a priori knowledge of the tracer (for example, knowledge of the distribution volume Vd of the tracer on a given population), on the imaged living organism 18 or on the conditions for performing the PET or SPECT examination (for example knowledge of the injected dose DI of tracer), etc.

They can be introduced in multiple ways into the estimation process, by setting or eliminating certain parameters from the equations, or in the form of additional terms in the cost function d, etc.

A second strategy consists of multiplying the estimates:
- with the same set of kinetics, i.e. the estimating step 34 is done several times for each set of kinetics determined in the determination step 30, as shown by the loop 52 in FIG. 2. This method makes it possible to reduce the bias but in a very limited way.
- with different sets of kinetics including I measured kinetics. Indeed, step 30 for determining a plurality of sets of kinetics makes it possible to generate at most $C_O^I$ sets of kinetics including the same number I of measured kinetics. The biases affecting the estimates from these sets of kinetics offset each other; and
- with different sets of kinetics including different numbers I of measured kinetics. As seen before, step 30 for determining a plurality of sets of kinetics makes it possible to generate at most $$\sum_{I=2}^{O} C_O^I$$

sets of kinetics. Here again, the biases affecting the estimates from these sets of kinetics offset each other.

A third strategy consists of proceeding with an iterative estimation, illustrated by the loop 54 in FIG. 2. In the first iteration, E input functions and E response functions of the regions of interest are estimated in the manner previously described. During subsequent iterations q, the $E_{q-1}$ input functions and the $E_{q-1}$ response functions of the regions of interest estimated in iteration q−1 serve either to determine the initialization of each of the $E_q$ estimates of the iteration q, or to contribute constraints to the estimate using the first strategy previously described.

Steps 32 for defining the kinetic model and 34 for estimating the input function and the pharmacokinetic parameters were described considering the known kinetic model.

Figure 5:
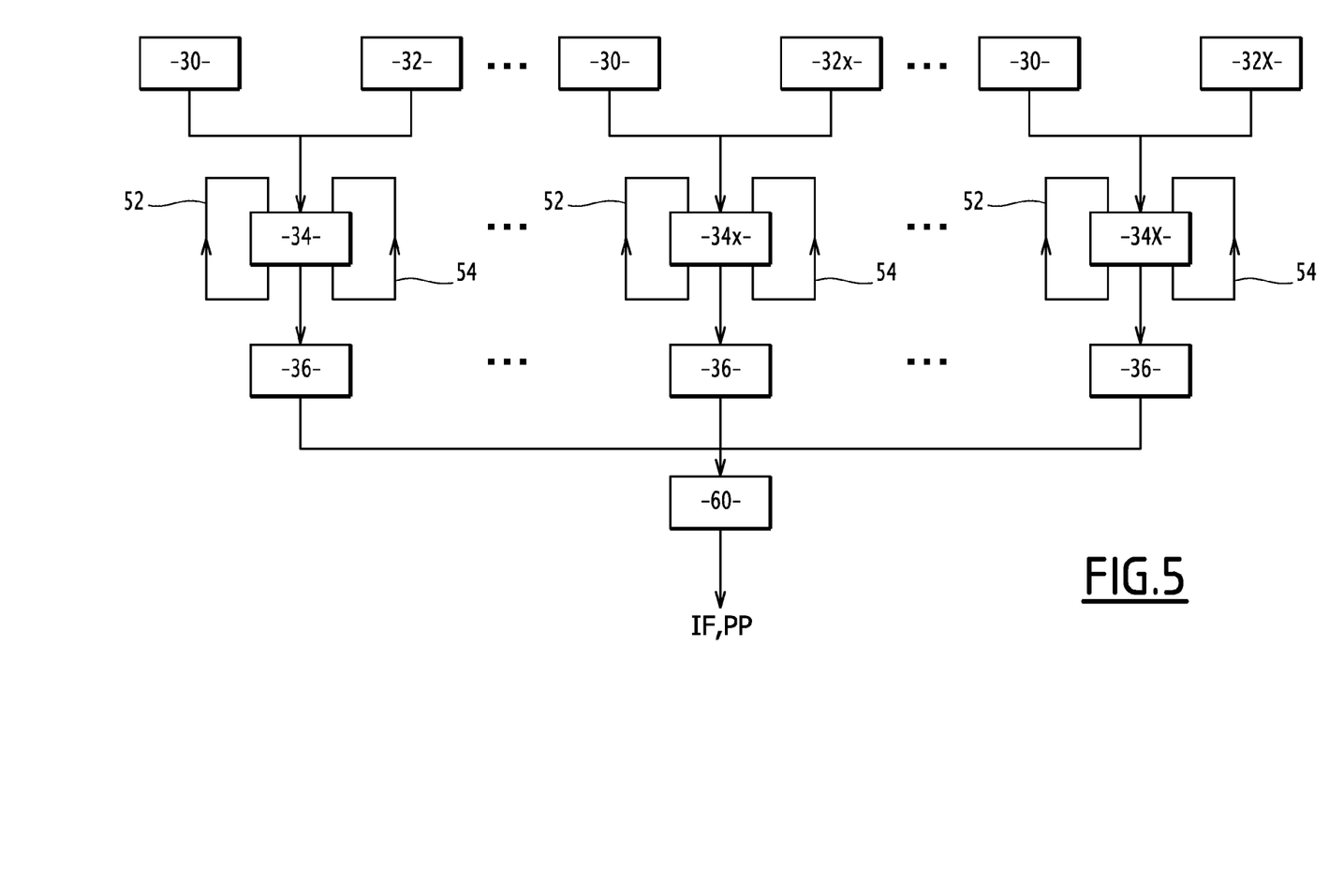
FIG. 5 is a flowchart showing additional steps of the inventive method.

In the case where said kinetic model is not known, whether it involves the pharmacokinetic behavior of the non-metabolized tracer and/or the pharmacokinetic behavior of any metabolites of the tracer, the method according to the invention makes it possible to estimate the input function and the pharmacokinetic parameters of the tracer while considering a plurality of kinetic models (FIG. 5).

To that end, the method comprises the definition of a plurality of kinetic models, parameters of the defined kinetic models being formed by the parameters of the input function and the pharmacokinetic parameters, as well as the resolution, for each determined set of kinetics, of the kinetic models defined from the determined set of kinetics.

More precisely, the method comprises as many additional steps 32x for defining a kinetic model as there are kinetic models being considered, x thus varying between 1 and X−1, X being the total number of considered kinetic models.

The method also comprises as many additional steps 34x for estimating the input function and the pharmacokinetic parameters as there are kinetic models being considered, x thus varying between 1 and X−1 and each additional step 34x making it possible to resolve a considered kinetic model.

The method comprises a step 60 for choosing, among the plurality of kinetic models defined in steps 32 and 32x, an optimal kinetic model in terms of compromise between suitability of the kinetic model to the data and the small number of parameters of the input function and the pharmacokinetic parameters to be extracted.

This selection step 60 is done using means 62 included by the device 10 (FIG. 1) and connected to the deducing means 24.

One example of an application of the inventive method in the context of a cerebral study in humans is described below.

A PET image of the brain of a human subject 18 is obtained by the imaging device 12 and partitioned into O regions of interest within each of which the kinetics of the tracer are measured.

The determination step 30 is carried out in the manner previously described and for example conducted at 100 sets of I kinetics, with $2 \leq I \leq O$.

This step 30 in particular makes it possible to avoid selecting a set of kinetics including several similar kinetics, for example kinetics resulting from the left hemisphere and from the right hemisphere, which are different assemblies but with similar functions.

Step 32 for defining a kinetic model proposes a model with three compartments: a vascular compartment and a tissue compartment which itself comprises two compartments, one where the tracer is free in the tissue and the other where it is specifically bonded.

Here we are considering a tracer having a single radio-marked metabolite that does not pass through the hematoenchephalic barrier, as is often the case in cerebral pharmacokinetic studies. The metabolite is then only present in the vascular compartment.

We also consider the case, which frequently arises, where the blood concentration is equal to the concentration in the artery.

We assume that the vascular fraction $Vb_i$ of the region of interest i has a density with a known Gaussian probability with mean $\mu_{Vb_i}$ and variance $\sigma_{Vb_i}^2$, measured on a sample of the population to which the imaged subject 18 belongs.

It is also assumed that the distribution volume Vd of the tracer has a density with a known Gaussian probability with mean $\mu_{Vd}$ and variance $\sigma_{Vd}^2$.

By including the metabolite in the kinetic model, this kinetic model in the region i is expressed by:

$$C_i(t) = Vb_i \times (Cp(t) + Ca_1(t)) + (1 - Vb_i) \times (Cp \otimes h_i)(t)$$

where $Ca_1$ is the concentration of the metabolite in the artery.

The response function of the region i to the non-metabolized tracer is expressed by:

$$h_i(t) = a_{i,1} e^{-b_{i,1} t} + a_{i,2} e^{-b_{i,2} t}$$

where $a_{i,1}$, $a_{i,2}$, $b_{i,1}$ and $b_{i,2}$ are expressed as known functions of the pharmacokinetic parameters $k_1$, $k_2$, $k_3$ and $k_4$.

For the input function, a parametric function is chosen with form:

$$Cp(t) = (A_1(t-\tau) - A_2 - A_3)e^{-\lambda_1(t-\tau)} + A_2 e^{-\lambda_2(t-\tau)} + A_3 e^{-\lambda_3(t-\tau)}$$

where $\tau$ is the time between the injection of the tracer and the beginning of the blood kinetics in the imaged viewing field.

The arterial concentration of the metabolized tracer is given by:

$$Ca_1(t) = \begin{cases} t < t_1 : 0 \\ t \geq t_1 : \alpha \times (1 - e^{-\beta(t-t_1)}) \end{cases}$$

Here, we consider the model as being known, so there are no additional steps $32x$ to perform.

In certain regions, the tracer can (a) not have a receptor, or even (b) build up without leaving the region. Case (a) corresponds to setting the parameters $a_2 = b_2 = 0$, and case (b) to setting $a_2 = b_1 = b_2 = 0$.

The estimating step 34 is then performed as follows.

Let $\{\Theta_j\}_{1 \leq j \leq J}$ be the set of parameters completely determining the shape of the input function, $\{\Phi_{i,k}\}_{1 \leq k \leq K}$ the set of parameters of the response function of the region i to the non-metabolized tracer, $\{\theta_{m,1}\}_{1 \leq l \leq L}$ the set of parameters completely determining the shape of the blood concentration of the metabolite m of the tracer and $\{\phi_{i,m,n}\}_{1 \leq n \leq N}$ the set of the parameters of the response function of the region i to the metabolized tracer.

We therefore have, for the input function:

$$\Sigma_1 = \tau, \Theta_2 = A_1, \Theta_3 = \lambda_1, \Theta_4 = A_2, \Theta_5 = \lambda_2, \Theta_6 = A_3, \Theta_7 = \lambda_3$$

For the response functions of the regions i to the non-metabolized tracer, we have:

$$\Phi_{i,1} = Vb_i, \Phi_{i,2} = a_{i,1}, \Phi_{i,3} = a_{i,2}, \Phi_{i,4} = b_{i,1}, \Phi_{i,5} = b_{i,2}$$

And for the model of the tracer, we have:

$$\theta_1 = t_1, \theta_2 = \alpha, \theta_3 = \beta, \{\phi_{i,m,n}\}_{1 \leq n \leq N} = 0$$

The quantity $A_1 + A_2$ is expressed as a function of the distribution volume Vd of the tracer and the injected dose DI of the tracer:

$$Vd = \frac{DI}{A_1 + A_2}$$

The estimation of the parameters $\{\Theta_j\}_{1 \leq j \leq 7}$, $\{\Phi_{i,k}\}_{1 \leq k \leq 5}$ and $\{\Theta_l\}_{1 \leq l \leq 3}$ from a set $\{Y_i\}_{1 \leq i \leq I}$ of I kinetics $Y_i$ determined in step 30, is done by minimizing the cost function d:

$$d(\{Y_i\}_{1 \leq i \leq I}, \{\Theta_j\}_{1 \leq j \leq 7}, \{\Phi_{i,k}\}_{1 \leq i \leq I, 1 \leq k \leq 5}, \{\theta_l\}_{1 \leq l \leq 3}) =$$

$$\frac{1}{I}\left(\sum_{i=1}^{I}\left(\frac{w_i}{T}\sum_{t=1}^{T} v_{i,t}(Y_i(t) - C_i(t))^2\right) + \delta_i \frac{(Vb_i - \mu_{Vb_i})^2}{\sigma_{Vb_i}^2}\right) +$$

$$\gamma \frac{\left(\frac{DI}{A_1 + A_2} - \mu_{Vd}\right)^2}{\sigma_{Vd}^2}$$

In this cost function d, $w_i$ is the gross collection ratio of the region i, i.e. the proportion of the signal effectively coming from the structure i that contributes to the average activity concentration measurements in the region i, accounting for the assignment of the kinetic $Y_i$ by the partial volume effect, $v_{i,t}$ is the variance of the error committed due to the statistical noise in the image on the estimate of $Y_i(t)$, $\delta_i$ and $\gamma$ are weights measuring the significance assigned to the a prioris, respectively on the vascular fractions of the regions and on the distribution volume of the tracer.

The parameters $\{\Theta_j\}_{1 \leq j \leq 7}$, $\{\Phi_{i,k}\}_{1 \leq i \leq I, 1 \leq k \leq 5}$, $\{\theta_l\}_{1 \leq l \leq 3}$ are for example estimated using the "Davidon-Fletcher-Powell variable-metric" algorithm proposed by the CERN in its ROOT library under the name "Migrad."

Step 36 for deducing the final input function and the final pharmacokinetic parameters is lastly performed. Once the set of E estimates is done, the final value of each parameter $\Theta_j$ of the input function and $\theta_l$ of the arterial concentration of the metabolite is chosen as the median of the E values estimated for that parameter.

The other parameters $\Phi_a$ are re-estimated as described for the estimating step 34, but by setting the parameters $\Theta_j$ of the input function and $\theta_l$ of the arterial concentration at said estimated final values, enabling a better estimation of the pharmacokinetic parameters.

Regarding the reduction of the bias on the estimated parameters, the system is constrained here by the choice of a parametric analytical form for the input function, but also for the kinetics of the metabolite in the artery.

The a priori knowledge of the vascular fractions $Vb_i$ of the regions i and the distribution volume Vd of the tracer introduced into the cost function d in the form of the terms $$\delta_i \frac{(Vb_i - \mu_{Vb_i})^2}{\sigma_{Vb_i}^2} \text{ and } \gamma \frac{\left(\frac{DI}{A_1 + A_2} - \mu_{Vd}\right)^2}{\sigma_{Vd}^2}$$

constrain the minimization.

If it is known that the concentration of the tracer is balanced between the vein and the artery, it is possible to add to the cost function d the term $$\varsigma \times \sum_{l=1}^{L} \frac{((Cp(t_l) + Ca_1(t_l)) - Cv(t_l))^2}{2 \times \sigma_v^2},$$

where Cv is the venous concentration of the tracer measured from the moment where the vein-artery balance is done and measured at L points with different times $t_l$, $\sigma_v^2$ is the uncertainty on the venous samples due to the statistical imprecision of the gamma counter, and $\varsigma$ is the weight measuring the importance assigned to the venous samples.

The venous samples must be differentiated from the arterial samples, the latter being much more difficult and uncomfortable for the imaged subject 18.

If it is possible to estimate the arterial kinetics $Ca_{meas}$ of the tracer (metabolized and non-metabolized) directly from the image and reliably, then the quantity $Cp(t) + Ca_1(t)$ can be replaced by $Ca_{meas}$ in the expression of the kinetic model $C_i(t)$, which makes it possible to decrease the number of parameters to be estimated by three. Once the other parameters are estimated, these three parameters related to the arterial concentration of the metabolite may be estimated by setting all of the other parameters.

The estimating step 34 is done several times for each set of kinetics, for example five times, in order to find the different solutions of the defined kinetic model that correspond to the different minimums of the cost function when it has several.

The determined sets of kinetics are all different from each other, some sets of kinetics including the same number I of measured kinetics and other sets of kinetics including a different number I of measured kinetics.

For example here, the number I of kinetics measured per set of kinetics varies between 3 and O, which corresponds to a maximum total number of $$\sum_{t=2}^{O} C_O^t$$

sets of kinetics, which yields 968 sets of kinetics for O=10 and 32647 sets of kinetics for O=15.

Such a large number of estimates is not necessary, because the precision gain by adding an additional set of kinetics decreases with the number of sets of kinetics already used. For example, the number of sets of kinetics can be limited to a maximum of 100.

Concerning the iterative estimation, the parameters to be extracted are estimated here in a single iteration.

When the kinetic model is not known, simplified kinetic models χ are tested using steps 32x and 34x.

Step 60 for choosing an optimal kinetic model then makes it possible to choose, among all of the tested models χ, the simplest model that best accounts for the physiological processes underlying the measured kinetics.

For example, the kinetic model chosen for each region i is the one verifying:

$$K = \underset{\chi}{\mathrm{argmax}} \Big( d\big(\{Y_i\}_{1 \le i \le I}, \{\Theta_j^{(\chi)}\}_{1 \le j \le J}, \{\Phi_{i,k}^{(\chi)}\}_{1 \le i \le I, 1 \le k \le K}, \{\theta_l^{(\chi)}\}_{1 \le l \le L}\big) \times \Big(J + L + \frac{I \times K}{2}\Big)\Big)$$

where $\{\Theta_j^{(\chi)}\}_{1 \le j \le J}$, $\{\Phi_{i,k}^{(\chi)}\}_{1 \le i \le I, 1 \le k \le K}$, $\{\theta_l^{(\chi)}\}_{1 \le l \le L}$ are the final parameters deduced in step 36 for the model χ, for the input function and for the region i.

The inventive method was tested on simulated data as well as on experimental data.

The simulated data is made up of N kinetics generated randomly according to a three compartment model and the chosen input function is a parametric input function as previously described.

The vascular fractions $Vb_i$ of the regions i are randomly drawn so as to remain plausible depending on the imaged subject 18. For cerebral studies, the vascular fractions are 1% (connective tissue), 2% (white matter), 3% (basal ganglia), and 4% (cortex), whereas for whole-body studies in rodents, the vascular fractions vary between 5% (muscle) and 10% (liver, lungs), or even 15% (kidneys) or 40% (heart).

The set parameters of the method (it will be recalled that it is mathematically impossible to estimate the input function and/or the pharmacokinetic parameters without setting certain parameters of the kinetic model) are the vascular fractions $Vb_i$ of the regions i, assumed to be known for the human brain and estimated over a population for rodents, as well as the time period τ between the injection of the tracer and the availability of the tracer to the regions i. This time τ is very short for rodents, but very long for humans.

Figure 6:
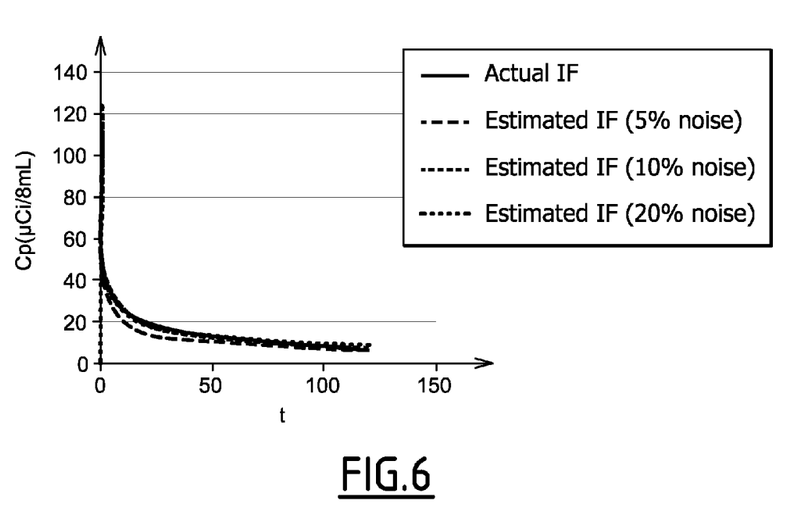
FIGS. 6 and 7 are diagrams showing the results obtained with the inventive method on simulated data for the input function and the pharmacokinetic parameters, respectively.

FIG. 6, which shows the results obtained for the input function for different noise values on simulated data of the human brain type and compares these results to the actual input function, indicates that the input function is indeed estimated regardless of the significance of the noise that affects the input kinetics, and without using venous and/or arterial samples.

The pharmacokinetic parameters K1, k2, k3 and k4 are randomly drawn in an interval consistent with the known values. For cerebral data, k4 was chosen to be small to simulate the examination kinetics of the FDG tracer.

Figure 7:
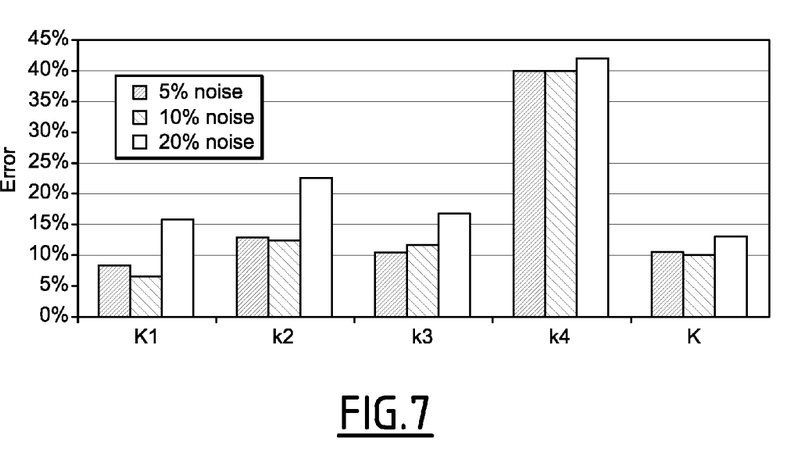

FIG. 7 shows the average relative error on each of the pharmacokinetic parameters as a function of the noise level with simulated data of the human brain type.

The significant relative error obtained on k4 is due to the very low value of that parameter, a small absolute error yielding a large relative error.

The macro-parameter K is a parameter making it possible to measure the regional glucose concentration:

regional metabolism of the glucose $$(CMRglu) = \frac{K_1 k_3}{k_2 + k_3} Cg_p / LC = K \times Cg_p / LC$$

where $Cg_p$ is the blood glucose concentration, easy to obtain by checking glycemia during the exam, and LC is the lumped constant that makes it possible to go from the K of the FDG model to the K of the glucose model.

The size $$K = \frac{K_1 k_3}{k_2 + k_3}$$

is therefore the main size of interest. An error of 10% on K is reasonable given that venous and/or arterial samples are not used.

The method has also been tested on experimental data of the human brain type and with the FDG tracer, and compared to arterial samples.

The vascular fractions $Vb_i$ of the regions i are set here at values assumed to be known, but should in reality be more precisely estimated to improve the results. The time period τ was set in the middle of the input of the PET signal in the brain. A more shrewd method of estimating tau must also be established to improve the results.

Figure 8:
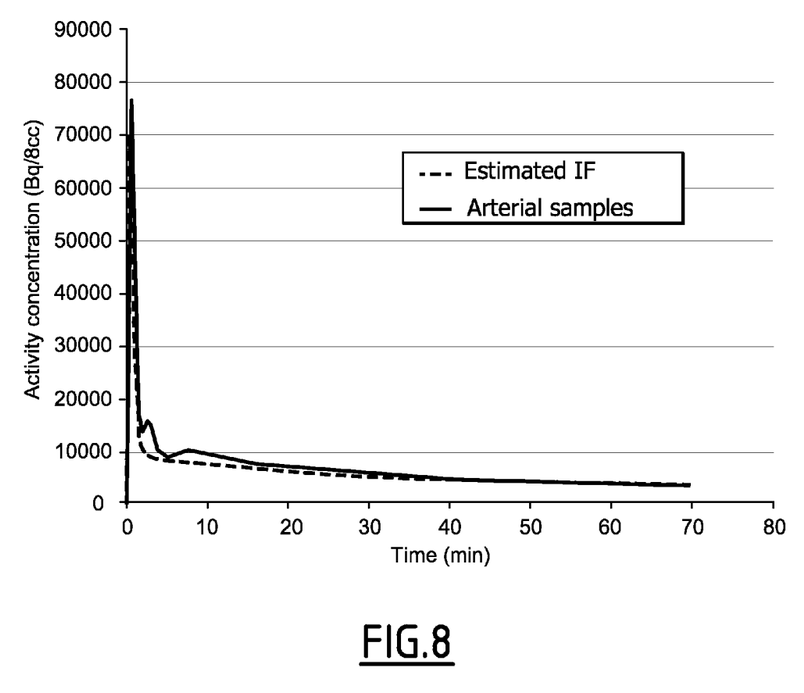
FIGS. 8 and 9 are diagrams similar to those of FIGS. 6 and 7, respectively, showing the results obtained on experimental data.

FIG. 8, which shows the results obtained for the input function on experimental data of the human brain type and compares those results to the actual input function obtained by arterial samples, which constitute the reference, indicates that the input function is indeed estimated, with a slight under-estimation in its central part, in particular at the time of the second peak of the input function corresponding to "syringe washing," peak that can be avoided if one does not need to precisely know the injected activity, the "syringe washing" consisting of adding physiological saline solution into the syringe and injecting it to push the residual tracer remaining in the catheters.

Figure 9:
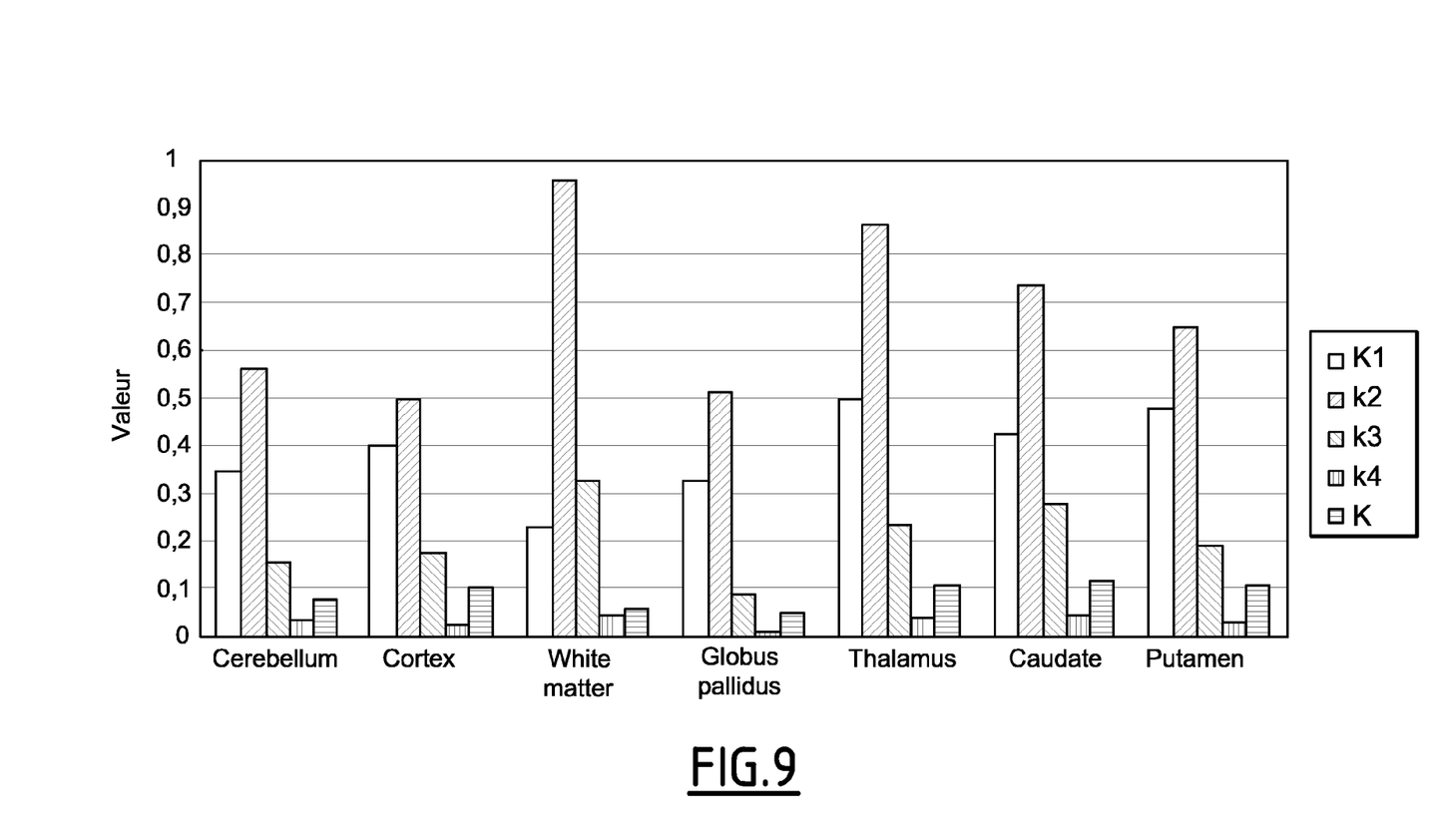

FIG. 9 shows the results obtained for each of the pharmacokinetic parameters as well as for the macro-parameter K with experimental data of the human brain type.

We do not have a reference here, but the parameters can be compared between regions. It appears reasonable for the factor K to be very close for the cortex, the thalamus, the caudate and the putamen, and lower for the white matter and the globus pallidus, with an intermediate value for the cerebellum.

On the other hand, the fact that K1 is lower for the white matter than for the cortex also appears plausible.

The invention therefore proposes a minimally invasive method that makes it possible to directly extract, from a measurement image of the kinetics of an active ingredient and with the smallest possible amount of bias, the input function simultaneously with the pharmacokinetic parameters of this active ingredient.

By minimizing a distance between several measured kinetics and the kinetics obtained as solution with a compartment model, by multiplying the estimations from a significant number of different sets of kinetics and by introducing a priori into the estimation other than arterial samples, the inventive method makes it possible to reduce the errors committed during an estimation and to thereby improve the robustness of the estimation.

Moreover, taking into account the pharmacokinetic behavior of any metabolites of the tracer makes it possible to apply this method to practically all existing and future tracers, both in whole-body studies and intracerebral or other organ studies.

Moreover, the inventive method makes it possible to modify the very nature of the information provided by the PET or SPECT exams and that is of interest to the practitioner (physician, pharmacologist, biologist, etc.), which will no longer only provide measurements of radioactivity, but directly the parameters of the model that underlies these radioactivity measurements.

Several medical applications can be contemplated: pharmacology, drug development, medical diagnostics, reduction of the number of tests, etc.

Pharmacology is a branch of medical research whereof the aim is to understand the effect of a drug on the body (pharmacodynamics) and the effect of the body on the drug (pharmacokinetics). It thus makes it possible to characterize pathologies, drugs and tracers. The obtainment of subtle pharmacokinetic parameters is an essential step in pharmacokinetics. The stakes of this method for pharmacokinetics are crucial, because arterial samples are done less and less for reasons related to safety and the comfort of the imaged subject.

About 39% of drugs do not reach the market for reasons related to poor pharmacokinetics. The obtainment of pharmacokinetic parameters as of the pre-clinical phase and at each step of the clinical phase could make it possible, with a great wealth of information and physiologically quantitative measurements, to dismiss or modify the candidate molecules as early as possible. This element is all the more crucial for the development of drugs as the development costs are currently remaining the same while fewer and fewer drugs are reaching the market, due to the increasing demands for scientific evidence and safety by the authorities.

The possibility of obtaining pharmacokinetic parameters without using arterial samples opens the doors to clinical diagnostics for pharmacokinetics. The consequences, in terms of indices, diagnostic sensitivity and specificity, have the potential to revolutionize the use of PET.

Directive 86/609/EEC regarding the protection of animals used for experimental and other scientific purposes requires that animal testing be as limited as possible. Whether it is done in humans or animals, the cost of a PET or SPECT test is also extremely high, and reducing the number of tests would be accompanied by a substantial reduction in the costs of medical research. However, it is known that, to measure a same effect of a drug with the same degree of certainty, the estimation of pharmacokinetic parameters makes it possible to reduce, by about one order of magnitude, the number of tests needed compared to a simple standard uptake value (SUV) measurement.

Figure 10:
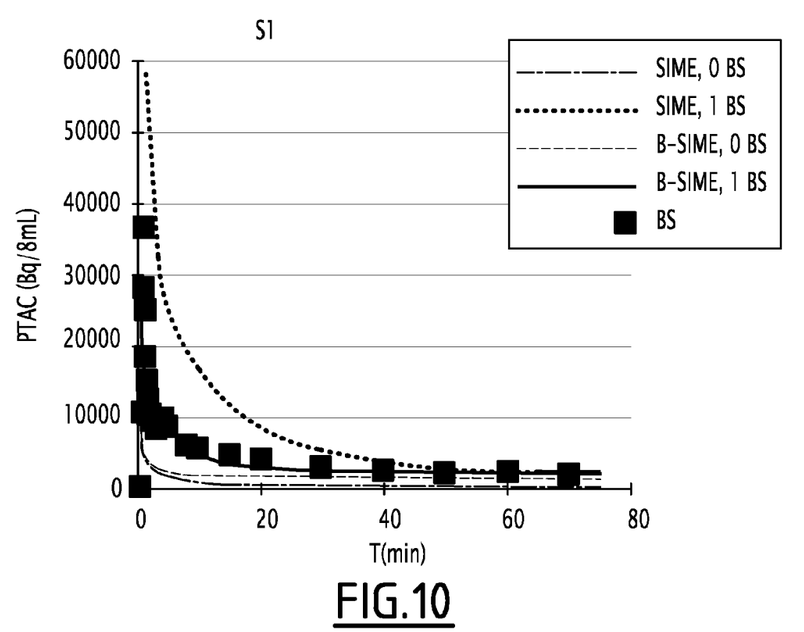
FIGS. 10 to 13 show the evolution of the activity in the arterial plasma of four subjects over time, according to different methods, including one method in an embodiment of the invention.

FIG. 10 shows the evolution of the activity in the arterial plasma (PTAC, Plasma Time Activity Curve) expressed in Bq/ML, for a healthy subject called S1, over a time T, expressed in minutes, according to different methods, including one method in an embodiment of the invention.

Figure 11:
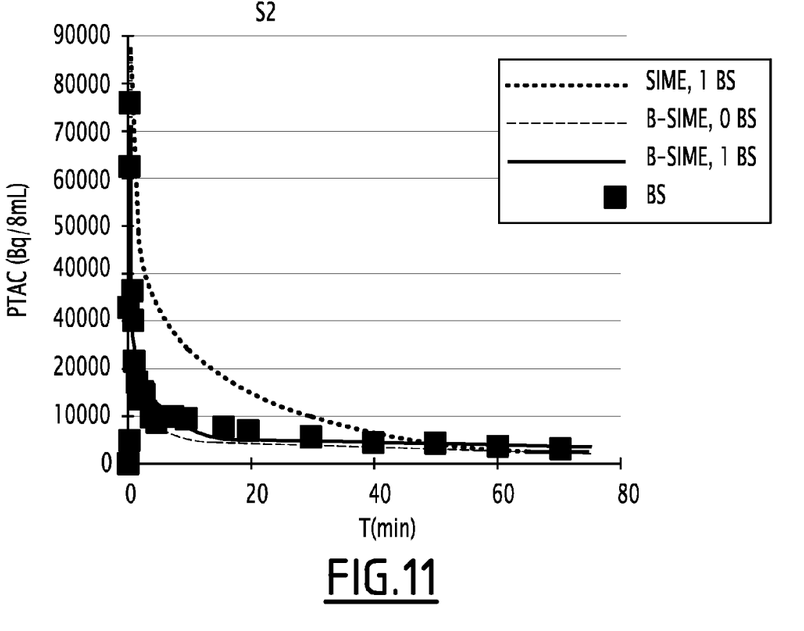
Figure 12:
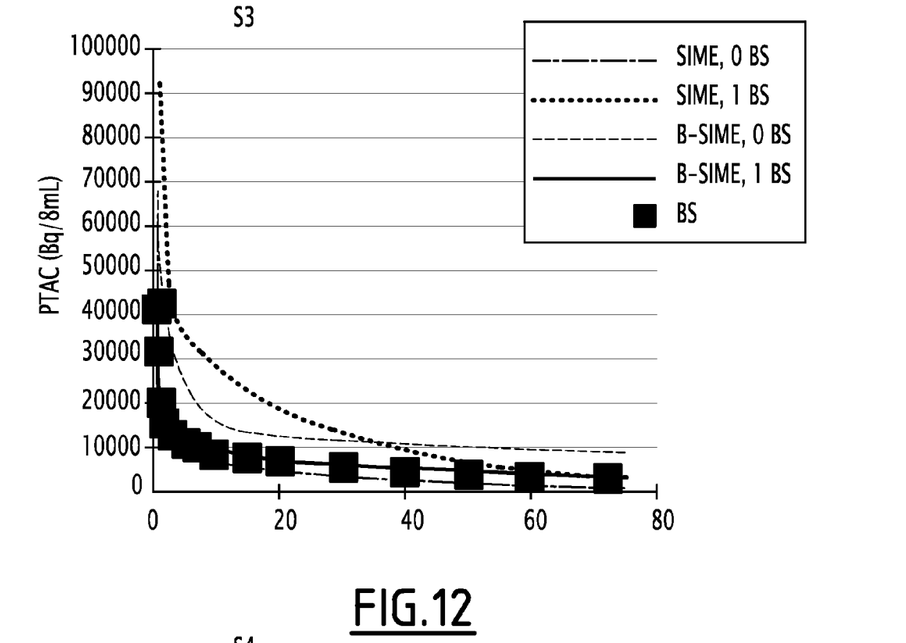
Figure 13:
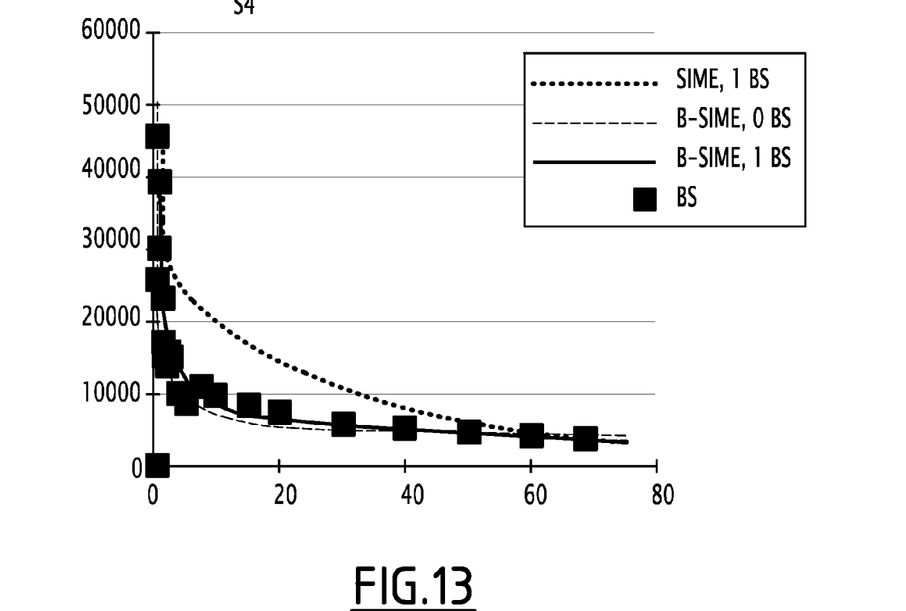

Similarly, FIGS. 11 to 13 show the evolution of the activity in the arterial plasma of respective healthy subjects S2, S3 and S4 over time, according to different methods, including one method in an embodiment of the invention.

The method in one embodiment of the invention, called B-SIME (Bootstrap approach for the SIME method) in FIGS. 10 to 13, was validated on 4 healthy subjects having had a PET (Position Emission Tomography) test, an MRI (Nuclear Magnetic Resonance Imaging), and arterial blood draws at the wrists during acquisition (BS for Blood Sample).

The SIME and B-SIME methods were compared on the four healthy subjects S1, S2, S3, S4 having undergone an MRI T1 on a GE Signa 1.5T imager and a PET test for one hour and ten minutes with a time slicing of 1×20 s, 10×10 s, 2×30 s, 2×2 min 30 s, 4×5 min, then 1×5 min at 50 min and 1×5 min at 1 h 5 min. The images were reconstructed using the OP-OSEM method with voxel of size 2.45×2.45×2.45 mm3. The MRI images were automatically segmented into 15 cerebral structures and corrected for the partial volume using the Geometric Transfer Matrix method (V. Frouin, JNM, 2002).

Blood samples were taken at irregular intervals (given here in minutes after the injection of the tracer). The SIME and B-SIME methods were compared on four healthy subjects having undergone an MRI T1 on a GE Signa 1.5T imager and a PET test for one hour and ten minutes with a time slicing of 1×20 s, 10×10 s, 2×30 s, 2×2 min 30 s, 4×5 min, then 1×5 min at 50 min and 1×5 min at 1 h 5 min. The images were reconstructed using the OP-OSEM method with voxel of size 2.45×2.45×2.45 mm3. The MRI images were automatically segmented into 15 cerebral structures and corrected for the partial volume using the Geometric Transfer Matrix method (V. Frouin, JNM, 2002).

The blood samples were taken at irregular intervals (given here in minutes after the injection of the tracer).

| Time (minute after injection) | | | |
| --- | --- | --- | --- |
| S1 | S2 | S3 | S4 |
| 0.15 | 0.07 | 0.10 | 0.10 |
| 0.35 | 0.20 | 0.30 | 0.25 |
| 0.47 | 0.30 | 0.40 | 0.35 |
| 0.62 | 0.42 | 0.58 | 0.48 |
| 0.78 | 0.52 | 0.83 | 0.60 |
| 0.97 | 0.63 | 1.07 | 0.72 |
| 1.12 | 0.73 | 1.37 | 1.07 |
| 1.28 | 1.00 | 1.53 | 1.18 |
| 1.43 | 1.12 | 1.68 | 1.32 |
| 1.58 | 1.40 | 1.87 | 1.63 |
| 1.82 | 1.67 | 2.03 | 1.77 |
| 2.01 | 2.08 | 2.23 | 2.02 |
| 2.70 | 2.62 | 2.52 | 2.52 |
| 3.01 | 3.02 | 3.10 | 3.00 |
| 3.97 | 3.87 | 4.33 | 4.00 |
| 4.80 | 5.07 | 5.20 | 5.42 |
| 7.70 | 7.57 | 7.38 | 7.53 |
| 9.53 | 9.58 | 9.78 | 10.00 |
| 14.87 | 15.70 | 14.88 | 15.17 |
| 19.97 | 19.78 | 19.52 | 20.17 |
| 29.75 | 29.93 | 29.80 | 30.13 |

-continued

| Time (minute after injection) | | | |
|---|---|---|---|
| S1 | S2 | S3 | S4 |
| 39.78 | 39.97 | 39.85 | 40.00 |
| 49.68 | 49.97 | 50.00 | 50.07 |
| 60.10 | 60.03 | 59.83 | 60.02 |
| 70.10 | 70.18 | 72.33 | 68.73 |

In all, 4 iterations were done with, for each iteration, 1,050 estimations: 300 with 3 organs per set of kinetics (OPJ), 250 with 4 OPJ, 200 with 5 OPJ, 150 with 6 OPJ, 100 with 7 OPJ and 50 with 8 OPJ, or a total of 4,200 estimations. At the end of each estimation, the parameters of the final input function were chosen to be equal to the median of the same parameters of the estimated input function weighted by a value taken at the minimum by the function to be minimized. The parameter having the lowest relative variation (Third Quartile—First Quartile)/Median at the end of an iteration is set for the following iteration.

The method according to the invention made it possible to find the arterial kinetics with good precision in each of the four subjects by using a single venous sample during the estimation, unlike the original SIME method (SIMultaneous Estimation of the input function and of the pharmacological parameters) in FIGS. 10 to 13), which systematically overestimates the arterial kinetics also with a venous sample.

The invention claimed is:

1. A method for simultaneously extracting the input function and pharmacokinetic parameters of an active ingredient in a structure of a living organism from a measurement image of the kinetics of the active ingredient in the structure obtained by an imaging device, the image comprising a plurality of regions of interest inside each of which the kinetics of the active ingredient are measured, comprising the following steps:
   determining a plurality of sets of kinetics from the measured kinetics, the determined sets of kinetics being different from each other and each determined set of kinetics including several measured kinetics;
   defining at least one kinetic model, parameters of the defined kinetics model being formed by parameters of an input function and pharmacokinetic parameters;
   estimating, for each determined set of kinetics, the input function and the pharmacokinetic parameters by resolving the kinetic model defined from the determined set of kinetics; and
   deducing a final input function and final pharmacokinetic parameters from estimated input functions and estimated pharmacokinetic parameters.

2. The method according to claim 1, wherein the step for determining the plurality of sets of kinetics comprises the following steps:
   forming all of possible sets of kinetics from the measured kinetics; and
   selecting, from the formed sets of kinetics, a predetermined number of sets of kinetics, this step comprising the following steps:
      evaluating, for each formed set of kinetics, a criterion for selecting sets of kinetics making it possible to assess their risk of introducing errors into the estimation of the input function and the pharmacokinetic parameters;
      ranking the formed sets of kinetics according to a rule of the maximum selection criterion; and
      choosing a predetermined number from the first ranked sets of kinetics.

3. The method according to claim 2, wherein the criterion for selecting sets of kinetics makes it possible to select the sets of kinetics whereof the measured kinetics are different from each other in terms of shape and/or amplitude, and/or whereof the measured kinetics are not very affected by the partial volume effect and/or whereof the measured kinetics have a strong signal to noise ratio.

4. The method according to claim one of claims 1 to 2, wherein the defined kinetic model takes into account the metabolization of the active ingredient in the structure of the imaged living organism.

5. The method according to any one of claims 1 to 2, wherein the step for estimating the input function and the pharmacokinetic parameters is done several times for each determined set of kinetics so as to find the different solutions for the defined kinetic model.

6. The method according to any one of claims 1 to 2, wherein the determined sets of kinetics comprise sets of kinetics including the same number of measured kinetics.

7. The method according to any one of claims 1 to 2, wherein the determined sets of kinetics comprise sets of kinetics including a different number of measured kinetics.

8. The method according to any one of claims 1 to 2, wherein the step for estimating the input function and the pharmacokinetic parameters comprises the minimization of a cost function making it possible to evaluate the dissemblance between the determined set of kinetics and the defined kinetic model.

9. The method according to any one of claims 1 to 2, wherein the step for estimating the input function and the pharmacokinetic parameters is carried out according to an iterative loop in which the input functions and pharmacokinetic parameters estimated during an iteration make it possible to determine the initialization of the input functions and pharmacokinetic properties estimated in the following iteration and/or to contribute constraints on the input functions and pharmacokinetic parameters estimated in the following iteration.

10. The method according to any one of claims 1 to 2, wherein:
   the step for defining at least one kinetic model comprises the definition of a plurality of kinetic models, parameters of the defined kinetic models being formed by the parameters of the input function and the pharmacokinetic parameters;
   the step for estimating the input function and the pharmacokinetic parameters comprises, for each determined set of kinetics, the resolution of the kinetic models defined from the determined set of kinetics,
   and the method comprises a step for choosing, among the plurality of kinetic models, an optimal kinetic model in terms of compromise between suitability of the kinetic model for the data and the low number of parameters of the input function and the pharmacokinetic parameters to be extracted.

11. The method according to any one of claims 1 to 2, wherein the step for defining at least one kinetic model comprises, aside from the choice of the form of the kinetic model, the introduction into the kinetic model of constraints resulting from a priori knowledge not related to arterial samples done on the imaged living organism, the constraints making it possible to set at least one parameter of the kinetic model such as the vascular fractions of the regions of interest.

12. The method according to any one of claims 1 to 2, wherein the step for estimating the input function and the pharmacokinetic properties comprises the introduction into the resolution of the kinetic model of constraints resulting from a priori knowledge not related to arterial samples done on the imaged living organism, the constraints making it possible to add known terms into the resolution of the kinetic model such as terms taking into account a priori knowledge of the vascular fractions of the regions of interest and/or the distribution volume of the active ingredient over a given population.

13. The method according to any one of claims 1 to 2, wherein the measurement image of the kinetics of the active ingredient in the structure is obtained from a temporal sequence of three-dimensional images obtained by position emission tomography or by single photon emission computed tomography.

14. A non-transitory information storage medium comprising a code for simultaneously extracting the input function and pharmacokinetic parameters of an active ingredient in a structure of a living organism from a measurement image of the kinetics of the active ingredient in the structure obtained by an imaging device, the image comprising a plurality of regions of interest inside each of which the kinetics of the active ingredient are measured, wherein the code comprises instructions to:

determine a plurality of sets of kinetics from the measured kinetics, the determined sets of kinetics being different from each other and each determined set of kinetics including several measured kinetics;

define at least one kinetic model, parameters of the defined kinetic model being formed by parameters of an input function and pharmacokinetic parameters;

estimate, for each determined set of kinetics, the input function and the pharmacokinetic parameters by resolving the kinetic model defined from the set of determined kinetics; and deduce a final input function and final pharmacokinetic parameters from estimated input functions and estimated pharmacokinetic parameters.

15. A device intended to simultaneously extract the input function and the pharmacokinetic parameters of an active ingredient in a structure of a living organism from a measurement image of the kinetics of the active ingredient in the structure obtained by an imaging device, the image comprising a plurality of regions of interest inside each of which the kinetics of the active ingredient are measured, comprising:

an imaging device; and a data processing system connected to the imaging device and comprising:

means for determining a plurality of sets of kinetics from measured kinetics, the determined sets of kinetics being different from each other and each determined set of kinetics including several measured kinetics;

means for defining at least one kinetic model, parameters of the defined kinetic model being formed by parameters of an input function and pharmacokinetic parameters;

means for estimating, for each determined set of kinetics, the input function and the pharmacokinetic parameters by resolving the defined kinetic model from the determined set of kinetics; and means for deducing a final input function and final pharmacokinetic parameters from estimated input functions and estimated pharmacokinetic parameters.

* * * * *